(12) United States Patent
Leroi et al.

(10) Patent No.: US 8,479,596 B2
(45) Date of Patent: Jul. 9, 2013

(54) DEVICE FOR SAMPLING A LIQUID IN A TUBE CLOSED BY A CAP

(75) Inventors: Pierre Leroi, Romily sur Andelle (FR); Benoit Lagarde, Sannois (FR)

(73) Assignee: Diagnostica Stago, Asnieres (FR)

( * ) Notice: Subject to any disclaimer, the term of this patent is extended or adjusted under 35 U.S.C. 154(b) by 531 days.

(21) Appl. No.: 12/744,578

(22) PCT Filed: Dec. 9, 2008

(86) PCT No.: PCT/FR2008/001714
§ 371 (c)(1),
(2), (4) Date: Aug. 23, 2010

(87) PCT Pub. No.: WO2009/103874
PCT Pub. Date: Aug. 27, 2009

(65) Prior Publication Data
US 2011/0120237 A1    May 26, 2011

(30) Foreign Application Priority Data

Dec. 13, 2007   (FR) .................................... 07 08689

(51) Int. Cl.
*G01N 1/14*   (2006.01)
*G01N 1/00*   (2006.01)
(52) U.S. Cl.
USPC ................... 73/863.83; 73/863.52; 73/864.86

(58) Field of Classification Search
USPC .................................. 73/863.83, 864.52, 863
See application file for complete search history.

(56) References Cited

U.S. PATENT DOCUMENTS

| | | | | |
|---|---|---|---|---|
| 4,274,453 | A | | 6/1981 | Lee |
| 5,173,265 | A | * | 12/1992 | Golias et al. ................... 422/550 |
| 5,216,926 | A | * | 6/1993 | Lipscomb ................... 73/864.25 |
| 5,380,486 | A | * | 1/1995 | Anami ............................. 422/63 |
| 5,400,666 | A | | 3/1995 | Song |
| 5,517,867 | A | * | 5/1996 | Ely et al. .................... 73/863.85 |
| 5,525,298 | A | * | 6/1996 | Anami ............................. 422/63 |
| 5,605,094 | A | * | 2/1997 | Besnier ....................... 100/70 R |

FOREIGN PATENT DOCUMENTS

| | | |
|---|---|---|
| EP | 0 520 796 A2 | 12/1992 |
| FR | 2 767 583 A1 | 2/1999 |
| FR | 2 810 407 A1 | 12/2001 |

OTHER PUBLICATIONS

International Search Report for Application No. PCT/FR2008/001714 mailed Sep. 21, 2009.

* cited by examiner

*Primary Examiner* — Hezron E Williams
*Assistant Examiner* — Rodney T Frank
(74) *Attorney, Agent, or Firm* — Alston & Bird LLP

(57) ABSTRACT

Device for sampling a liquid in a tube by means of a hollow needle (10) passing through the closing cap (12) of the tube (14), means (18, 20) with rack and toothed wheel being provided to oppose the rising of the tube (14) when the needle is extracted from the cap (12).

10 Claims, 3 Drawing Sheets

DEVICE FOR SAMPLING A LIQUID IN A TUBE CLOSED BY A CAP

FIELD OF THE INVENTION

The invention relates to a device for sampling a liquid in a tube closed by a cap, by means of a hollow needle that is made to pass through the cap and which is connected to means of suction, for the sampling of a determined quantity of the liquid contained in the tube.

This known technique of sampling through the cap of a tube has the advantage of making it possible to carry out the sampling without opening of the tube, therefore by limiting the risks of contamination, on the one hand, of the liquid contained in the tube and, on the other hand, of the environment of the tube.

Of course, the invention applies to the devices for sampling a liquid in recipients of any type closed by caps or similars and is not limited to the sampling of liquid in a tube. In order to simplify the description, the application of the invention shall be described with a sampling of liquid in a tube closed by a cap, although it is applicable to all types of recipients closed by caps or similars through which a sampling needle can be made to pass.

BACKGROUND OF THE INVENTION

Typically, the closing cap of the tube comprises a septum which can be passed through without difficulty by the sampling needle while providing a seal around the needle, and wherein the hole of passage of the needle closes in a sealed manner when the needle is extracted from the tube.

However, during the withdrawal of the needle, the friction of the needle in the hole of passage formed in the cap tends to raise the tube and to remove it from its means for support and positioning, with the risks of breakage of the tube and also risks of the loss of identification of the sample contained in the tube, when the means for identifying are borne by the support of the tube.

In order to avoid these disadvantages, it has already been proposed to provide such a sampling device with means for immobilising of the tube, which press against the periphery of the cap or on the upper end of the tube when the needle is descended through the cap and which then retain the tube and prevents it from raising again with the needle as long as the latter is not entirely withdrawn from the cap.

These known means include a ring or a part bearing on the cap, this ring or this part being mounted at the lower end of a rack which is guided in vertical translation in a bearing borne by a support element. The rack cooperates with a catch for immobilising and blocking which is solicited towards the rack by a spring mounted on the support element in such a way that the rack can descend into the bearing until the ring or the bearing part is placed on the cap or on the upper end of the tube, the rack then being blocked in this position by the catch which prevents it from rising back as long as the spring is not separated from the rack by a transversal finger which is mounted on the support of the needle and which accompanies the latter in its upward movement.

This known system of tube immobilisation has several disadvantages resulting substantially from the wear and tear of the catch on the teeth of the rack during the descent of the latter, risks of sliding of the catch on the teeth of the rack and of the vertical positioning by pitch of the rack in relation to its catch and to its support.

SUMMARY OF THE INVENTION

This invention has for purpose in particular to eliminate these disadvantages.

It proposes to this effect a device for sampling a liquid in a tube closed by a cap, comprising a needle displaced in translation by motor means to pass through the cap of the tube, means for immobilising the tube which can be displaced with the needle in order to press against the cap or the upper end of the tube when the needle is descended through the cap, means for blocking means for immobilising when the needle is raised back through the cap, and means for unblocking means for immobilising when the needle is out of the cap, characterised in that the means for blocking include a toothed wheel mounted rotating about a stirrup by the intermediary of a unidirectional rotation mechanism, said stirrup being mounted pivoting around an axis between a first position wherein the toothed wheel is engaged with a rack parallel to the direction of displacement of the needle and a second position wherein it is separated from this rack, with the unidirectional rotation mechanism of the toothed wheel authorising, when the toothed wheel is in the first position, a descent of the means for immobilising, and prohibiting in this first position the rising of the means for immobilising.

Thanks to the cooperation of the rack with the toothed wheel with unidirectional rotation, the positioning of the bearing part on the cap no longer depends on the pitch between the teeth of the rack. In addition, there is no possibility of sliding of the toothed wheel in relation to the teeth of the rack and the wear and tear of the toothed wheel is very low since it is distributed across all of the teeth on this wheel.

As such, the means for blocking according to the invention are effective when the means for immobilising fastened to the rack are pressing against the cap or on the upper end of the tube, without it being required to proceed with any adjusting whatsoever to this effect. Then, the only required adjustment relates to the travel of the rising of the needle which will make it possible to unlock the means for immobilising.

According to another characteristic of the invention, the centre of gravity of the stirrup and of the toothed wheel is off centre in relation to the fixed axis of rotation in such a way that the toothed wheel is brought by gravity into its first position.

As such, no means for biasing the toothed wheel into its position of blocking of the rack is required.

Moreover, any effort exerted on the means for immobilising and tending to raise it when the rack is engaged with the toothed wheel, results in a spin torque exerted on the stirrup of the toothed wheel which maintains and reinforces the pressing of the toothed wheel on the teeth of the rack. The system formed by the toothed wheel and the rack is therefore self-locking.

According to other characteristics of the invention:
the means for unblocking include a transversal lug fastened to the needle and pressing against, when the needle is out of the cap, on the stirrup of the toothed wheel in order to pivot it around the fixed axis and bring the toothed wheel into its second position;
this transversal lug bears a contact roller bearing with the stirrup of the toothed wheel;
the pivoting axis of the stirrup of the toothed wheel is mounted on a steady bearing in translation mounted on the rack;
the rack and the steady bearing are immobilised in rotation in relation to one another by a roller bearing borne by the bearing and engaged on the rack.

All of these means contribute to reducing the wear and tear of the device according to the invention and to increasing its simplicity, its operating safety and its life span.

In a first embodiment of the invention, the rack is fastened to the means for immobilising while the steady bearing is mounted on a fixed support.

In a second embodiment, the rack is borne by a fixed support and it is the steady bearing which is fastened to the means for immobilising.

This second embodiment has the advantage that the device according to the invention can be used with tubes of different heights and automatically adapts to the various heights of tubes.

BRIEF DESCRIPTION OF THE DRAWINGS

The invention shall be better understood and other characteristics, details and advantages of the latter shall appear more clearly when reading the following description, given by way of example in reference to the annexed drawings wherein.

DETAILED DESCRIPTION

Figure 2:
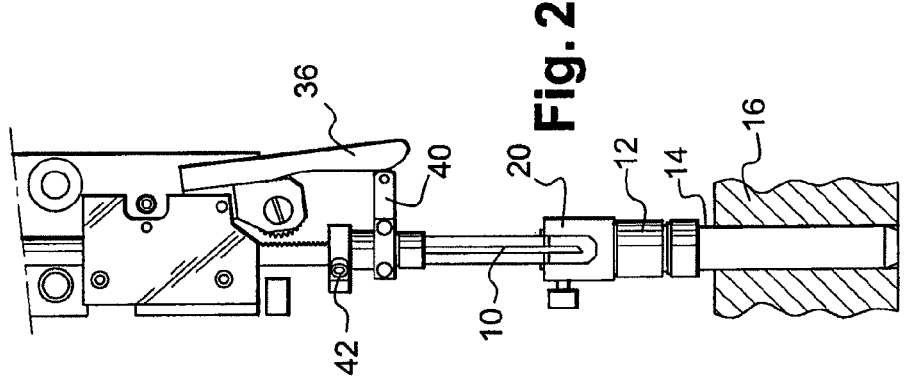
FIGS. 1 and 2 diagrammatically show a sampling device according to the invention, in sampling position and in position of unblocking respectively.
Figure 1:
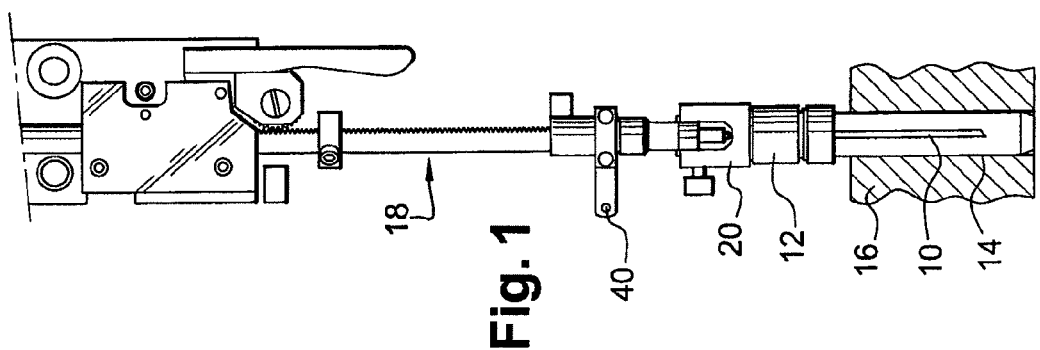

The device for sampling a liquid shown diagrammatically in FIGS. 1 and 2 comprises a hollow needle 10 that can be displaced in vertical movement by motor means in order to pass through in a sealed manner a cap 12 for closing a tube 14 containing a liquid, such as for example a biological sample to be analysed, this cap being of the septum type or comprising a septum.

The tube 14 is placed in a housing of a means of support 16 of any suitable type.

The needle 10 is connected at its upper end to means of suction for the sampling of a determined quantity of the liquid contained in the tube 14.

Figure 3:
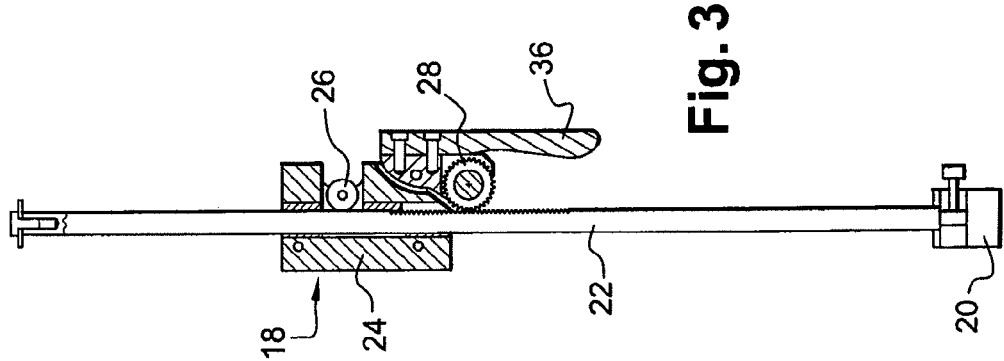
FIG. 3 diagrammatically shows the means for tube immobilising according to the invention.

The immobilisation of the tube 14 in its housing is provided by means 18 which are parallel to the needle 10 and to its means of displacement and which include a bearing part 20 on the cap 12, this part 20 comprising an orifice for the passage of the needle 10 and being mounted at the lower end of a vertical rack 22 guided in translation in a bearing 24 which comprises (FIG. 3) a roller bearing 26 mounted in rotation around a horizontal axis and received in a vertical groove of the rack 22 in order to prohibit the rotation of the rack around its longitudinal axis in the bearing 24.

This bearing is itself borne by a device for sampling which, generally, can be displaced in a horizontal plane above the tube 14 or a series of tubes 14 mounted in the support 16.

Figure 4:
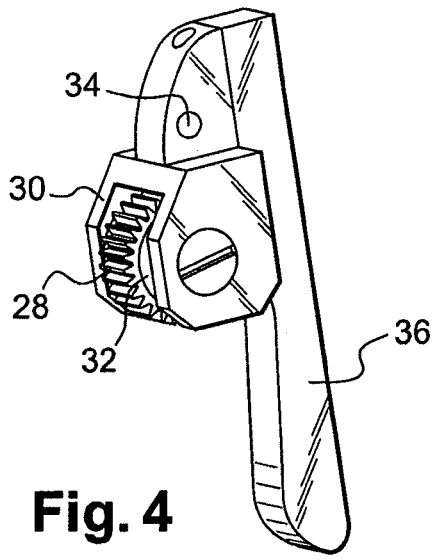
FIG. 4 is a diagrammatical view in perspective of the toothed wheel and of its support stirrup.
Figure 5:
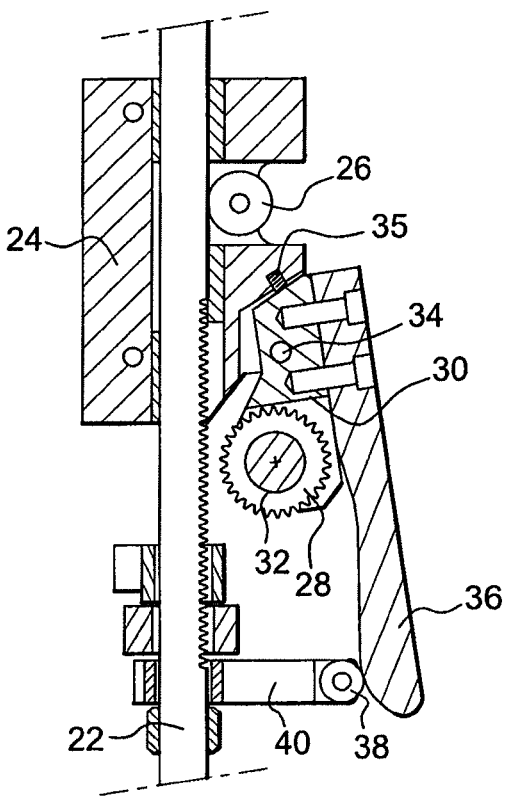
FIG. 5 is a diagrammatical view showing the unblocking of the means for immobilising the tube.

The means for immobilising 18 also include means for blocking the rack 22, these means for blocking being formed substantially of a toothed wheel 28 (FIGS. 3, 4 and 5) which is mounted in rotation around a horizontal axis in a stirrup 30 by the intermediary of a unidirectional rotation mechanism 32. The stirrup 30 is itself mounted pivoting at its upper end around a horizontal axis 34 on the bearing 24 of the rack in such a way as to automatically bring, by gravity, the toothed wheel 28 engaged with the rack. A compression spring 35 mounted on the bearing 24 presses against the stirrup 30 in order to provide a constant pressure of the toothed wheel 28 on the rack 22 and prevent the "bounce back" phenomena when the means 18 are in descending phase.

On its longitudinal side opposite the toothed wheel 28, the stirrup 30 bears or comprises an extended cam 36 which extends downwards and which is intended to cooperate with a rotating roller 38 mounted at the end of a horizontal finger 40 which is fixed on the support of the needle 10 and which accompanies the rising of this needle in such a way that, when the roller 38 comes into contact with the cam 36 when rising, it pushes this cam towards the right in the drawing and causes the stirrup 30 to pivot around the axis 34 anti-clockwise by separating the toothed wheel 28 from the rack 22.

The finger 40 is positioned perpendicularly in relation to the needle 10 in order to come into contact with the cam 36 as shown in FIG. 2 when the needle is already out of the cap 12 of the tube 14. After having actuated the cam 36, the finger 40 comes into contact with a stop 42 which is secured to the rack 22, in order to raise the bearing part 20 which remained on the cap 12, which then makes possible a horizontal displacement of the device without touching the tubes which are in the vicinity.

The device according to the invention operates in the following manner:

it is first displaced in a horizontal plane in order to bring the needle 10 above a tube 14, then the needle 10 descends towards this tube. Simultaneously, the part 20 borne by the lower end of the rack 22 is applied to the cap 12, the descending of the rack being authorised by the toothed wheel 28 engaged with the teeth of the rack and by the unidirectional rotation mechanism associated with the toothed wheel.

The needle 10 then passes through the cap 12 and, in the position in FIG. 1, allows for the sampling of a determined quantity of the liquid contained in the tube 14.

Figure 6:
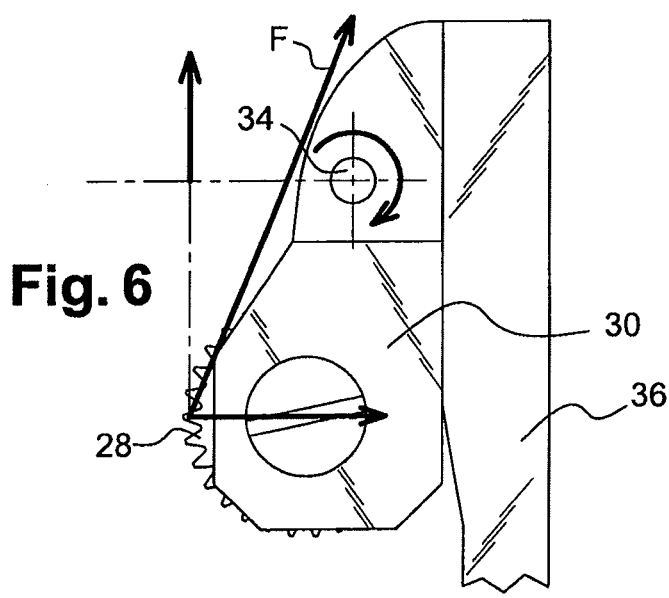
FIG. 6 is a diagram of the forces acting on the toothed wheel during the rising of the needle.

Then, the needle is raised and extracted from the cap 12 as shown in FIG. 2, with the part 20 being maintained against the cap 12 of the tube, by the toothed wheel 28 of which the rotation is prohibited and which blocks the rising of the rack 22. In this position, the result F of the forces exerted by the rack 22 on the teeth of the toothed wheel 28 is directed upwards and passes on the left of the pivoting axis 34 (FIG. 6) in such a way that a spin torque is exerted on the stirrup 30 in the direction indicated by the arrow, in order to maintain the toothed wheel 28 engaged with the rack.

When the rising of the needle 10 is such that the finger 40 reaches the cam 36, the stirrup 30 pivots around the axis 34 anti-clockwise and the toothed wheel 28 is removed from the rack 22. This rack will then accompany the needle in its rising and release the tube 14, due to the pressing of the finger 40 on the stop 42.

During the following use of the device for sampling a liquid, when the needle is descended towards the cap 12 of a tube 14, the rack 22 descends by gravity and the bearing part 20 mounted at the lower end of the rack presses against the cap of the tube.

This embodiment of the invention is applicable in the case where the tubes of a series of tubes placed in the support 16 all have the same height.

Figure 7:
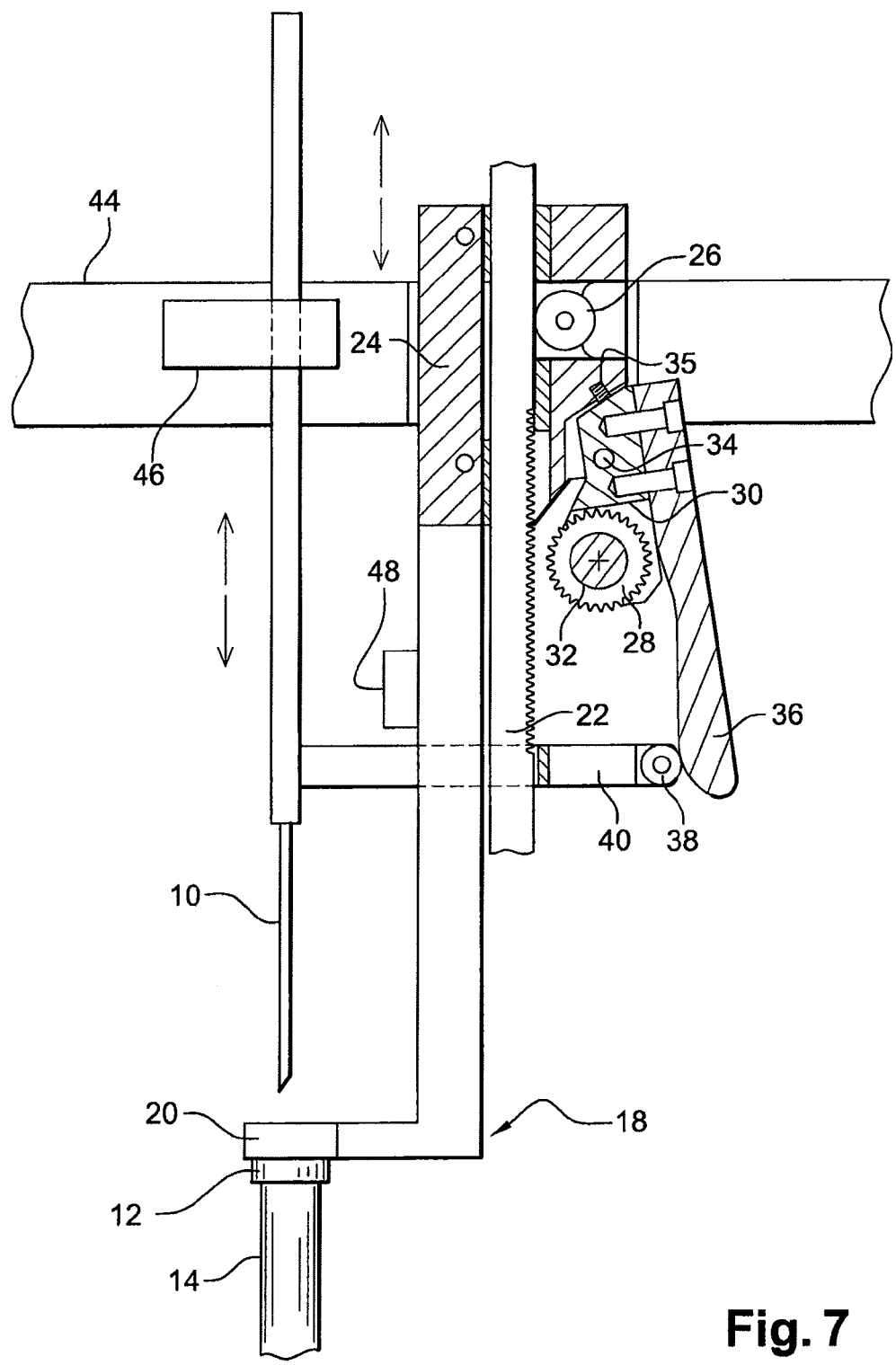
FIG. 7 diagrammatically shows an alternative embodiment of the invention.

The embodiment shown in FIG. 7 can be used with tubes 14 that have different heights. It differs from the embodiment in FIGS. 1 to 6 in that the rack 22 is fixed and mounted on a fixed support 44 which also bears motor means 46 for vertical displacement of the needle 10, while the bearing 24 is guided in translation on the rack 22 and bears the means for immobilising 18 comprising the bearing part 20 on the cap 12 of a tube 14.

In this embodiment, the unidirectional rotation mechanism 32 of the toothed wheel 28 makes it possible to descend the bearing 24 along the rack and opposes its rising, when the toothed wheel 28 is engaged with the rack 22.

The device in FIG. 7 operates in the following manner:

When the needle 10 is in upper position, the finger 40 fixed on the support of the needle presses against a block 48 which is fastened to the means for immobilising 18 and maintains the latter in upper position, where the bearing part 20 is separated from the cap 12 of a tube 14.

In this position, the toothed wheel 28 is separated from the rack 22 by the cam 36 pressing against the roller 38 of the finger 40.

When the needle 10 is descended towards the cap 12 of the tube, it allows the means for immobilising 18 to descend with it until the part 20 is pressing against the cap 12 as shown in FIG. 7.

Then, when the needle 10 is still descended, the finger 40 releases the cam 36 and the toothed wheel 28 becomes engaged with the rack 22.

The needle 10 is driven into the cap 12 for a sampling of liquid in the tube 14.

When the needle 10 is extracted from the cap, the bearing part 20 is maintained on the cap of the tube because the mechanisms 32 opposes the rotation of the toothed wheel 28 in the direction of the rising of the bearing 24.

The needle 10 continues rising until the finger 40 comes to stop against the cam 36 and separates the toothed wheel 28 from the rack 22. Then, the rising of the needle 10 causes the rising of the bearing 24 by pressing of the finger 40 on the block 48 of the means for immobilising 18.

In this device, the rising of the means for immobilising 18 by pressing of the finger 40 on the block 48 does not depend on the height of the tube 14 and always occurs after separation of the toothed wheel 32, regardless of the height of the tube, with the device adapting automatically and without adjustment to all tube heights.

The invention claimed is:

1. Device for sampling a liquid in a tube closed by a cap, comprising a needle displaced in translation by motor means in order to pass through the cap of the tube, means of immobilising the tube which can be displaced with the needle in order to press against the cap when the needle is descended through the cap, means for blocking means for immobilising when the needle is raised through the cap and means for unblocking means for immobilising when the needle is out of the cap, wherein the means for blocking include a toothed wheel mounted rotating about a stirrup by the intermediary of a unidirectional rotation mechanism, said stirrup being mounted pivoting around an axis between a first position where the toothed wheel is engaged with a rack parallel to the direction of displacement of the needle and a second position where it is separated from this rack, the unidirectional rotation mechanism of the toothed wheel authorising, when the toothed wheel is in the first position, a descending of the means for immobilising and prohibiting in this first position the rising of the means for immobilising.

2. Device according to claim 1, wherein the centre of gravity of the stirrup of the toothed wheel is off centre in relation to the axis of rotation of the stirrup in such a way that the toothed wheel is brought by gravity into its first position.

3. Device according to claim 2, the stirrup is solicited by a spring in rotation around the axis in a direction pressing the toothed wheel on the rack.

4. Device according to claim 1, wherein the means for unblocking include a transversal finger displaced by the needle in order to come and press, when the needle is out of the cap, against the stirrup of the toothed wheel and pivot this stirrup around the axis of rotation in order to bring the toothed wheel into its second position.

5. Device according to claim 4, wherein the transversal finger bears a contact roller bearing with the stirrup of the toothed wheel.

6. Device according to claim 1, wherein the pivoting axis of the stirrup of the toothed wheel is mounted on a steady bearing in translation on the rack.

7. Device according to claim 6, wherein the rack and the steady bearing are immobilised in rotation in relation to one another by a roller bearing mounted in the bearing and engaged on the rack.

8. Device according to claim 6, wherein the steady bearing is mounted on a fixed support and the rack is fastened to the means for immobilising.

9. Device according to claim 6, wherein the rack is mounted on a fixed support and the steady bearing is fastened to the means for immobilising.

10. Device according to claim 1, wherein the means for unblocking include means for raising means for immobilising when the needle is out of the tube.

* * * * *